United States Patent [19]
Hays et al.

[11] Patent Number: 5,855,791
[45] Date of Patent: Jan. 5, 1999

[54] PERFORMANCE-BASED CONTROL SYSTEM

[75] Inventors: George Hays, Morristown; John Haaland, Dover, both of N.J.

[73] Assignee: Ashland Chemical Company, Dublin, Ohio

[21] Appl. No.: 610,146

[22] Filed: Feb. 29, 1996

[51] Int. Cl.⁶ .............................. C02F 5/00; G05D 21/00
[52] U.S. Cl. .................... 210/696; 137/3; 137/5; 137/88; 137/93; 210/96.1; 210/143; 210/198.1; 210/739; 364/500; 364/502; 422/7; 422/111
[58] Field of Search ............................ 210/87, 96.1, 143, 210/167, 198.1, 696, 739, 746, 764, 805; 436/6; 422/7, 14, 53, 62, 110, 111; 137/1–3, 5, 87, 93, 88; 364/496, 497, 500, 502, 510, 550, 509; 73/61.76; 162/3

[56] References Cited

U.S. PATENT DOCUMENTS

| | | | |
|---|---|---|---|
| 3,592,212 | 7/1971 | Schleimer | 137/93 |
| 3,918,469 | 11/1975 | Zamboni et al. | 137/5 |
| 4,339,945 | 7/1982 | Knudsen et al. | 422/53 |
| 4,346,587 | 8/1982 | Brindak | 422/53 |
| 4,464,315 | 8/1984 | O'Leary | 137/93 |
| 4,648,043 | 3/1987 | O'Leary | 364/502 |
| 4,659,459 | 4/1987 | O'Leary et al. | 210/96.1 |
| 4,830,757 | 5/1989 | Lynch et al. | 210/96.1 |
| 5,242,602 | 9/1993 | Richardson et al. | 210/143 |
| 5,360,549 | 11/1994 | Mouche et al. | 210/143 |

*Primary Examiner*—Joseph W. Drodge
*Attorney, Agent, or Firm*—Pollock, Vande Sande & Priddy

[57] ABSTRACT

A method for detecting and controlling cooling system characteristics. A flow rate of make-up cooling medium is measured. A conductivity of the make-up cooling medium is measured. A conductivity of a recirculating cooling medium is measured. A treatment material feed rate is determined based upon the formula:

$$X = \frac{(\text{make-up cooling medium flow rate})(\text{make-up cooling medium conductivity})(\Omega)}{(K)(\text{recirculating cooling medium conductivity})},$$

where X is a treatment feed rate of a treatment compound, $\Omega$ is a desired concentration of the treatment compound, and K is a constant. A corrosion rate of the recirculating cooling medium is measured. A desired corrosion rate of the recirculating cooling medium is determined. A feed rate of a corrosion inhibitor is calculated according to the following formula:

$$Y = (X)[1 + \alpha(\text{CORR}_{MEASURED}/\text{CORR}_{SETPOINT})],$$

where $\alpha$ is a cascade factor that varies in a step-wise manner depending upon the value of $\text{CORR}_{MEASURED}/\text{CORR}_{SETPOINT}$ and has a value between about 0.1 and about 8.0. A corrosion inhibitor is then fed at the corrosion inhibitor feed rate.

28 Claims, 1 Drawing Sheet

PERFORMANCE-BASED CONTROL SYSTEM

FIELD OF THE INVENTION

The invention relates to systems, including method and apparatus, for controlling chemical treatment and water quality within cooling systems by measuring corrosion and fouling to adjust treatment control parameters in the cooling systems.

BACKGROUND OF THE INVENTION

The purpose of a cooling system is to remove heat from a process and discharge that heat to the environment through evaporation and liquid discharge. An example of such systems are cooling water systems used to remove heat from a turbine-condenser. Removing the heat causes steam to condense, resulting in a pressure reduction on the steam-condensate side of the condenser, and an increase in the amount of power generated per unit of fuel used to produce the steam. Similarly, another example of such a system is a refrigeration machine. Such a machine may utilize a refrigerant, such as R-11, R-12 or R-134A, to extract heat from a chilled medium, such as water, loop and transfer the heat to a cooling system.

Another example of a cooling system is one in which heat from a process or series of processes may be transferred to the cooling medium through a process heat exchanger, such as an intercooler on an gas compressor. The operating efficiency of a multi-stage gas compressor, such as an oxygen or nitrogen compressor, may be directly tied to the temperature and pressure of the gas stream entering each stage of the compressor. The higher the temperature and pressure above design conditions, the more power will be required to compress the same amount of gas.

According to one example of a cooling system, the cooling medium includes a liquid, such as water. Such a cooling system may comprise (1) at least one heat exchanger for removing heat from one or more processes; (2) at least one pump for circulating the cooling medium through the at least one heat exchanger; (3) means for cooling the cooling medium, such as a cooling tower; (4) means for adding new cooling medium to the system, such means is typically referred to as makeup; and (5) means for discharging a certain amount of cooling medium from the system, such discharge is referred to as blowdown.

The cooling effect according to such a system may be achieved by evaporating a fraction of the cooling medium into a stream of air as the cooling medium passes over the cooling tower. During the process of removing heat from the cooling medium, unsaturated air may enter the cooling tower. The unsaturated air may pick up the evaporated fluid and exit the cooling tower at a higher temperature and in a saturated state with respect to the cooling medium.

According to another example of a cooling system, a cooling medium, such as water, may be obtained from a large reservoir of the medium that will provide an adequate supply of the cooling medium at a temperature low enough to absorb heat from a process or processes via at least one heat exchanger. In such an example, the cooling system may include (1) a source for the cooling medium; (2) means for circulating the cooling medium, such as at least one circulating pump; (3) at least one heat exchanger; and (5) a place to discharge the heated cooling medium, such as the same body of cooling medium as the source.

Cooling systems that employ liquid cooling media may be subject to deposition of foulant materials and processes, such as, hardness salts, corrosion products, biomass, silt, and mud from the cooling medium, various process leaks, and in-situ corrosion. These foulant materials and processes may be input into the cooling systems from a variety of sources.

Certain treatment materials may be added to the cooling medium or cooling system to inhibit, among other things, hardness deposition, corrosion, formation of biomasses, and agglomeration of other foulants such as silt, mud, corrosion products and process leaks. Such treatment materials may include one or more chemical components that, in combination, effectively inhibit one or more of the above mentioned problems. For example, a treatment material designed to inhibit corrosion may include at least one cathodic inhibitors, at least one anodic inhibitors, and/or at least one additional materials, such as anti-scalants, surfactants and anti-foam agents. Other treatment materials that may be added to the system/medium may include an acid, such as sulfuric acid, or an alkali, such as a solution of caustic soda. These additional materials may control the Ph of the cooling medium within a predetermined control range. When controlling the pH, the acid would be used to lower the pH and the alkali to raise it.

Typically, the amount of treatment material(s) added to the system/medium may be determined by manual laboratory tests, corrosion coupon analyses, the volume of cooling medium in the system and the amount of cooling medium supplied to the system in a given period of time. In such cases, means, such as a chemical injection pump, may be used for injecting a flow of a treatment material into the system at a constant rate over time.

When adding material(s) to adjust pH, a closed loop chemical injection system may be utilized. For example, the system pH may be monitored by a pH monitoring device that controls a pump or valve to increase or decrease the feed of the pH adjusting agent(s).

Treatment materials used to inhibit the deleterious effects of process leaks are typically controlled manually, either on a continuous basis or upon detection of the occurrence of such a leak. Detecting, locating and quantifying a process leak is a time consuming task that may be performed by a plant operator or treatment professional.

Another important aspect of treatment and control of a cooling system and the quality of the cooling medium relates to maintaining the concentration of dissolved and suspended materials in the medium below the level at which they may precipitate or agglomerate. This is typically accomplished by adjusting the amount of concentrated cooling medium removed from the system via blowdown. Typically, this has been done by manual adjustment of a blowdown valve, based on laboratory analysis of the circulating cooling medium. More recently, blowdown has been automated by monitoring the specific conductivity of the cooling medium and adjusting a blowdown valve to maintain a specified range of conductivity.

Typically, a cooling system includes a cooling medium, such as water. The characteristics or properties of the cooling medium may affect the cooling system and its operation. Cooling medium parameters such as pH, conductivity, corrosion rates, temperatures (such as cold supply, hot return, heat exchanger inlet, and outlet, among others), cooling medium recirculation rate, cooling medium make-up rate and cooling medium blowdown rate have long been monitored to control the characteristics of cooling medium. Blowdown may serve to deconcentrate the dissolved solids in the cooling medium and the makeup replaces all cooling medium losses, including those from evaporation, windage, drift and blowdown. Historically, automated control of cooling systems has been based upon on-line measurements of conductivity and pH, for example. Measurements of these factors may be supplemented by laboratory wet chemistry tests for residual inhibitor level and other parameters relevant to the specific application. In some cases, particularly where side-stream filtration is used, turbidity monitoring has been added.

The use of linear polarization resistance technology for on-line measurement of corrosion rates was previously disclosed in U.S. Pat. Nos. 3,069,322, 3,156,631, 3,250,689, 3,607,673 and No. 3,698,065, the entire disclosures of all of which are hereby incorporated by reference. In U.S. Pat. No. 4,339,945, to Knudsen, and U.S. Pat. No. 4,346,587, to Knudsen et al., the entire disclosures of both of which are hereby incorporated by reference, a methodology was disclosed where in a device in which the measurement of fouling added to pH, conductivity and corrosion is disclosed and applied to determine the effectiveness of a treatment regime in inhibiting corrosion and fouling in fluid systems, such as cooling water. Since corrosion may decrease the economic life of equipment in the cooling system and fouling may reduce the efficiency of heat rejection from plant processes to the cooling medium, it is very important to keep these under control.

Traditional control of open recycling cooling systems typically includes the use of a single loop controller for controlling the pH with either an acid, such as sulfuric acid, or a base, such as a solution of caustic soda. A single loop controller may be included for controlling the level of dissolved solids in the cooling medium. Such dissolved solids may be measured by specific conductivity, and may be increased or decreased via adjusting a blowdown, or bleed off valve. Increasing the rate of bleed off may cause the dissolved solids in the cooling medium to decrease. Some type of feed control for treatment chemicals may also be utilized for controlling the characteristics of cooling systems. Calendar date and time combined with an interval timer function are commonly utilized in control of systems and, in particular, for adding various types of microbicides.

Control of pH and conductivity typically utilizes feedback control technology. Feedback control may provide either analog or digital outputs to operating equipment such as pumps and valves. Analog outputs may go through Proportional Integral Derivative (PID) controllers for more precise control. Make-up medium flow rate, the flow rate of cooling medium added to the system compensate for medium lost to evaporation and other losses, such as windage and blowdown, is typically the basic control parameter for feed of treatment chemicals such as inhibitors and dispersants. In a cooling system, and an aqueous cooling system in particular, the make-up medium may be water supplied from at least one source, such as potable municipal water, well water, reclaimed process water, externally treated water, and condensate. Another commonly used, but less precise, method is to use the blowdown medium flow rate, which requires an assumption that other liquid losses may be either fixed or proportional to blowdown. A third means is called "bleed and feed", which proportions the addition of treatment materials to the time that an on/off, for example, a solenoid, bleedoff or blowdown valve is actuated.

Linear Polarization Resistance (LPR) technology has been used for nearly three decades to monitor corrosion rates on-line. This technology is marketed as a "CORRATER" monitor by Rohrback Cosasco Systems, Inc. The analog signals provided by the CORRATER monitor are proportional to the "instantaneous" corrosion rate or the "instantaneous" corrosion imbalance. In fact, the CORRATER monitors determine the LPR over a period of time that may be as little as about 2 minutes or as long as about 20 minutes. Thus "instantaneous" is a relative term when compared with off-line techniques, which may require about 30 to about 90 days of coupon exposure.

Fouling Factor (FF) is a recognized engineering unit of measure. The FF results from the deposition of foulants on a heat transfer surface. The P-U-L-S-E analyzer, available from Ashland Chemical, Drew Industrial Division, provides the ability to determine the FF The ONGUARD CFM-1000 monitor, also available from Ashland Chemical, Drew Industrial Division, determines a Fouling Index (FI). Research has proven that FI and FF have identical trends, yet they are numerically different and are computed in different manners.

Known methods of monitoring characteristics of cooling systems and controlling parameters of the systems may be of three types. The first type of include those that have traditionally lent themselves to automated feedback control of certain parameters, such as pH for the control of acid or caustic feed and conductivity for the control of bleedoff or blowdown.

The second type are those that detect the residual of a specific component in the treatment chemistry where such can be adequately measured in such a stream of the cooling medium. There are two known approaches to this type of monitoring. The first approach includes detecting a single active component, while the second type of detecting includes detecting an inert material that acts as a tracer.

Phosphate monitors are examples of the first approach to detecting since they detect only a single species of phosphorous ion, orthophosphate, in the cooling water system. In fact, the treatment chemistry may include several different phosphorous bearing materials together with various polymers, aromatic azoles and other constituents.

In the presence of calcium, magnesium, ferrous and ferric ions, orthophosphates have limited solubility. The limited solubility is a complex function of pH, temperature and ionic concentration. In some systems, the solubility of such materials under operating temperatures and pressures may be close to the desired control limits making it difficult to differentiate between an excessive feed and conditions that may lead to deposition and, ultimately to underdeposit corrosion.

Use of an inert trace compound that, unlike the active materials, can be detected in the stream of the cooling medium has its own shortcomings because it may only tell the user how much trace material is in the system. It may be unable to determine the efficacy of the treatment. For example, a treatment material, such as active constituents in a corrosion inhibiting composition, typically are consumed by reaction(s) in the process of inhibiting corrosion, or whatever process they are directed to inhibiting. The remaining treatment material is that portion that the reaction(s) do not consume and/or residual portion(s) that are required to sustain the involved reaction(s) by driving them to completion. Inert material(s), on the other hand, pass through the system without substantially reacting with anything. The above discussion may apply to any treatment material.

Other monitoring techniques include off-line monitoring such as complete chemical and microbiological analysis of the circulating water and analysis of corrosion coupons.

SUMMARY OF THE INVENTION

The present invention overcomes problems in the prior art, providing a performance based control system that integrates key performance detection, including fouling and corrosion, into a control system. As such, it is truly unique and a significant enhancement of the prior art.

In view of the above, it is an object of the present invention to adjust the chemical treatment of the cooling medium to control corrosion and fouling at economically acceptable levels in order to maintain efficient heat rejection and protect the economic life of the cooling system equipment.

One advantage of the present invention is that it is based on direct measurement of the effects of fouling and corrosion, for example, of treatment and control, as opposed to monitors and controllers that measure and control based upon tracers or other chemical species that may form one component of a multiple component treatment material.

Another advantage of the present invention is that the invention replaces traditional single loop control technologies with integrated control, utilizing multiple input measurements and logic to control single outputs plus adding cascade control to integrate fouling and corrosion.

In accordance with these and other objects and advantages, preferred aspects of the present invention provide a method for detecting and controlling cooling system characteristics. A flow rate of make-up cooling medium is measured. A conductivity of the make-up cooling medium is measured. A conductivity of a recirculating cooling medium is measured. A treatment material feed rate is determined based upon the formula:

$$X = \frac{\text{(make-up cooling medium flow rate)}\text{(make-up cooling medium conductivity)}(\Omega)}{(K)\text{(recirculating cooling medium conductivity)}},$$

where X is a treatment feed rate of a treatment compound, $\Omega$ is a desired concentration of the treatment compound, and K is a constant. A corrosion rate of the recirculating cooling medium is measured. A desired corrosion rate of the recirculating cooling medium is determined. A feed rate of a corrosion inhibitor is calculated according to the following formula:

$$Y = (X)[1 + \Omega(\text{CORR}_{MEASURED}/\text{CORR}_{SETPOINT})],$$

where $\alpha$ is a value between about 0.1 and about 8.0.

According to other preferred aspects, the present invention provides an apparatus for detecting and controlling conditions in a cooling system. The apparatus includes means for measuring a flow rate of a make-up cooling system medium. The apparatus also includes means for measuring a conductivity of the make-up cooling system medium. Additionally, the apparatus includes means for measuring a conductivity of a recirculating cooling medium. The apparatus further includes means for determining a treatment material feed rate based upon the formula:

$$X = \frac{\text{(make-up cooling medium flow rate)}\text{(make-up cooling medium conductivity)}(\Omega)}{(K)\text{(recirculating cooling medium conductivity)}},$$

where X is a treatment feed rate of a treatment compound, $\Omega$ is a desired concentration of the treatment compound, and K is a constant.

Still other objects and advantages of the present invention will become readily apparent those skilled in this art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

DETAILED DESCRIPTION OF THE INVENTION

The present invention may employ traditional technologies and known parameters described above to control a cooling system. However, in addition to or instead of these traditional technologies and known parameters, the present invention utilizes both Linear Polarization Resistance (LPR) corrosion rates and Fouling Index (FI) in control schemes. In addition, the present invention is based on a basic material balance technology that maintains a predetermined concentration of treatment chemistry in the recirculating cooling medium. The present invention may also be useful for controlling oxidizing microbicides in a cooling system medium.

To control conditions in a cooling system, the present invention may include means to monitor time dependent variables of fouling and corrosion in a method to adjust treatment control parameters. Notwithstanding the above, some of the measurements that the control is based upon may be instantaneous. The parameters may include, but are not limited to, pH, conductivity, cycles of concentration, oxidation-reduction potential (ORP), and turbidity to optimize heat rejection efficiency and minimize deterioration of materials of construction resulting from corrosion and fouling. In basing a control system upon fouling and corrosion, the present invention expands upon known technology by developing a cascade-based process control methodology that utilizes fouling and corrosion measurements to adjust operating parameters to minimize the deleterious effects of both and to assure optimization of cooling system performance. Further, the sensitivity of this methodology is a significant improvement over all other available technologies.

According to the present invention, changes in parameters of a cooling system may be monitored and controlled by monitoring corrosion and fouling factor. Materials that are added to the cooling system to adjust the parameters may then be controlled by adjusting a feed rate of the materials. According to the present invention, it has been found that corrosion rate and Fouling Index may be used as a means to modify chemical feed rates and other controlled parameters, such as blowdown rate, which, in turn, alters cycles of concentration. Accordingly, the present invention is based on a cascade control. Therefore, similarly to controlling cooling medium pressure to control cooling medium temperature, the present invention uses corrosion and fouling to control other parameters.

The basic material balance algorithm takes the following formula:

$$X = \frac{\text{(make-up cooling medium flow rate)}}{(K)(\text{recirculating cooling medium conductivity})},$$

where:

X=feed rate of a treatment material;

Ω=desired concentration in circulating cooling medium; and

K represents a constant. The value of K may be adjusted depending upon the measurement of the flow rate. If the flow is measured in gallons per minute and it is desired that X be expressed in pounds per minute, K would be about 120,000. On the other hand, if flow is measured in cubic meters per hour and it is desired that X be expressed in kilograms per hour, then K would be about 1,000. Other values of K may be calculated easily, based upon the various units utilized.

Typically, in cooling systems, the treatment material feed rate is measured in pounds per one million pounds of makeup medium required to maintain a desired concentration of treatment material. Also, Ω is typically measured in mg/l. However, the units may vary, depending upon the size of the cooling system, parameter, and/or treatment material, among other factors.

The value of Ω may depend upon the expected chemistry of the cooling medium in the operating system and the chemical composition of the product. Typically, Ω will be different for every treatment product. Also, the value of Ω may be increased or decreased for a specific combination of product and system based on extensive experience with a particular cooling system.

The formula for X is a basic calculation that could be used by one skilled in the art of cooling medium treatment to compute the treatment chemical feed rate based on maintaining a specific concentration in the circulating cooling medium. An alternate means to make that calculation is used where plants cannot measure the quality of makeup cooling medium, but instead use the blowdown cooling medium flow rate. In that case, the calculation would be:

$X=(\Omega)(\text{Cooling Medium Blowdown Flow Rate})/(120,000)$

Either method provides the basic feed rate for the treatment product.

In control logic, X is determined by an open loop system, that is, the actual concentration of the treatment product in the circulating cooling medium is not measured by the control system. In this case, Ω is the reference input to the control loop which regulates the rate at which the treatment material is fed, X. Ω may be adjusted as function of a second, but unrelated variable, called the cascade function discussed in detail below. The cascade function may be α, for corrosion rate, or β, for Fouling Index.

As discussed above, the corrosion rate may be factored into the above calculation for material feed rate by use of a cascading function that provides a step-wise increase in treatment feed rate in order to maintain a corrosion rate within allowable limits. The calculated cascade factor values may be used to increase the feed rate for the specific product by multiplying X by the Cascade Factor to determine the adjusted feed rate Y. For example, in an open recirculating cooling medium system, it is desired to maintain a corrosion rate equal to or less than 3 mils per year (MPY) on mild steel, for example American Institute of Steel Industries (AISI) 1010, as measured by a CORRATER monitor.

The corrosion rate cascade function is typically applied as a step-wise factor, according to the following table:

| $CORR_{MEASURED}/CORR_{SETPOINT}$ | Cascade Factor (α) |
|---|---|
| <0.75 | 0.00 |
| 0.75–0.99 | 0.15 |
| 1.00–1.50 | 0.40 |
| 1.50–3.00 | 1.00 |
| >3.00 | 2.00 |

The values above are only examples of the cascade factors that may employed. Additionally, all values are approximate and may vary from the above without departing from the invention.

The cascade factors shown in the above table are dimensionless empirically determined factors based on field experience and laboratory data. The values may be a function of the product chemistry, system design and operating conditions and/or a combination thereof. For example, in a heat exchanger where the cooling medium is on the shell side, the fluid velocity is normally very slow. If the heat duty of such a heat exchanger is such that the surface temperature is high, for example, greater than about 140° F, the potential for both fouling and corrosion is very high. The chemistry of some corrosion inhibitor products may, in high concentrations, actually increase the Fouling Index, while other products may have little or no effect. Therefore we may use values of approximately 1.00, 1.10, 1.25, 1.5 and 1.8 for the cascade factors.

In some cases, such as when an aromatic azole is used specifically to inhibit corrosion of copper and copper bearing alloys, the cascade factor may be approximately 0.6, 1.0, 2.0, 4.0 and 8.0, respectively. This is partially due to the fact that normally, the corrosion rates are so low on such metals, for example, less than about 0.2 MPY, and that upsets, when they occur, are potentially severe. However, the aromatic azole has no deleterious effect on fouling. Another issue is cost effectiveness. For example, aromatic azoles are very expensive and normally used in very low dosages.

An example involving the use of aromatic azoles involves a power generating station. The station employs chlorine on a periodic basis, for example, about once every approximately two days, as an oxidizing microbicide to inhibit the accumulation of biomass. Typically, a copper alloy corrosion rate is below about 0.2 MPY. However, during the application of chlorination, corrosion rates for the copper may exceed 20 MPY. While the elevated corrosion rate may last only about a few hours, the elevated rate might have been lowered if the control system had the ability to adjust the aromatic azole dosage level for period of chlorination.

As an alternative, the corrosion rate cascade function may be applied as an algorithm to continuously adjust the corrosion inhibitor as a function of the difference between the corrosion rate "set-point" and the actual corrosion rate such as:

If $CORR_{MEASURED} > CORR_{SETPOINT}$, then $Y=(X)[1\alpha(CORR_{MEASURED}/CORR_{SETPOINT})]$, where:

α=an empirically determined numerical value between about 0.1 and about 2.0 and Y=corrosion inhibitor feed rate.

According to the invention, a similar type of cascade control may be used to adjust for Fouling Index (FI). Fouling Index is a time dependent phenomenon. Fouling Index is a dimensionless number that may be calculated based on a bulk temperature of the cooling medium, temperature of a wall between a heat source and the stream of cooling medium, a flow rate of the stream of cooling medium as it passes a heated surface, a power level associated with the heated surface, and factors for converting a measured rate of flow of the cooling medium into a value for fluid velocity and shear stress against the heated surface.

Base line data for calculating the Fouling Index may be obtained under clean conditions to set the starting point or zero FI. The Fouling Index may then be calculated according to the formula below. After acquiring the base line data, values may periodically be sensed for the above-listed variables and the Fouling Index calculated for each sensing time. Periodic sensing of the variables and recalculation of the Fouling Index permits measurement of the FI under operating conditions. The time period between sensing may vary. Typically, the time may be as short as a few seconds or as long as an hour. Research has shown that under normal fouling conditions, readings taken at intervals of about thirty (30) seconds to about five (5) minutes provide optimal results. However, in cases of severe fouling, shorter time intervals may be warranted. For example, time intervals as short as from about thirty seconds to about one minute have been utilized. In conditions of negligible fouling, time intervals may be longer. For instance, intervals about fifteen to about thirty minutes have been employed. While longer time periods may be used, the usefulness of intervals greater than thirty minutes may be a function of the system design and operating conditions. However, typically, the longer the interval, the less sensitive the control will be to changes in Fouling Index. Thus, while longer intervals are possible, they may not be utilized as often.

The Fouling Index may be calculated according to the following formula:

$$FI = (A)\{[(T_w - T_b)/Power - B]_c - [(T_w - T_b)/Power - B]_i\} + J,$$

where $$J = (C)[(T_b)_c - (T_b)_i)] + (D)\ (F_c - F_i) + (E)(POWER_c - POWER_i)$$

F=flow rate,
J=correction factor,
Power=power
$T_b$=bulk fluid temperature,
$T_w$=wall temperature,
i represents initial readings,
c represents current readings, and
A, B, C, D, and E represent correction factors.

The value of correction factors A, B, C, D, E, and J may vary, depending upon the application and the desired affect of the treatment materials, the rate of addition of which may be affected by the value of the Fouling Index. For example, correction factor A may be between about 0.002 and about 1000. According to one preferred embodiment, correction factor A is about 400.

Correction factor B may be used to adjust for changes in flow rate. Correction factor B may be especially good for compensating for small changes in flow rate. Correction factor B may consider the total value of the flow rate. Correction factor B may vary from about 0.167/F to about 1/F According to a preferred embodiment, correction factor B may be about 0.25/F.

In one embodiment, correction factors C, D, and E have values of about 0.321, about 1.432 and about 0.0665, respectively. However, the values of each of these factors may vary, depending upon the embodiment and the application, among other factors. For example, while C may have a value of from about 0.2 to about 0.7, D may have a value of from about 0.9 to about 1.85, and E may have a value of from about 0.03 to about 0.13.

In one embodiment, A has a value of about 400, B has a value of about 0.25/F, C has a value of about 0.321, D has a value of about 1.432, and E has a value of about 0.0665.

The formula for the value of J is the result of a series of calibration runs. The formula for correction factor J preferably includes terms that correct for changes in bulk cooling medium temperature, flow, and power. Correction factor J may be calculated based upon the change in conditions between base data and latest reading. Although other values for correction factor J may be used, a value calculated according to the above formula may "normalize" the data by eliminating the remaining noise.

The value of any of the correction factors, and particularly correction factor A may vary, depending upon how a user desires to scale the calculated values. Additionally, the Fouling Index may also be corrected without using one or more of the correction factors. However, a correction factor may be desirable to eliminate "noise" in the calculation. That is, without a correction factor, the amplitude of the noise may exceed the change in value of the Fouling Index. Further, the value of the Fouling Index may be adjusted using the correction factors to help ensure that anomalous high and/or low values do not cause adverse reactions and contribute to fouling problems if, for example, the resulting concentration of treatment material is too high.

Economics may also play a role in the application of the of the calculated Fouling Index. For example, a heat exchanger designer may set different fouling allowances for different heat exchangers, thus establishing different levels of fouling tolerance for them.

As another example of the role that economics may play a role in the operation of a cooling system, economic limits of the operator, whether at the level of an individual or a corporation, of the cooling system may decide that certain conditions will be economically acceptable. As an illustration, in one case, an older plant that is scheduled for closing in a few years may find a high corrosion rate to be acceptable. Thus, the operator of that plant may choose to limit the maximum concentration of corrosion inhibitor materials by limiting the amplitude factor or raising the set point.

Although other algorithms exist for calculating the above terms, including FI, they differ mostly by modifications that could alter the numeric results. Such alterations could include changing the normalization. For example, the value of the correction factors could be varied.

Control of FI may be based on two factors, first $FI_{ACTUAL}$ versus $FI_{SETPOINT}$ and second, the rate of change of FI with time ($\Delta FI/\Delta t$) once equilibrium is reached with the fluid environment. Both step-wise and continuous adjustment of control bias are applicable to such systems.

For example, if $FI_{ACTUAL} > FI_{SETPOINT}$ then, $$Z = (X)[1 + (\beta)(FI_{ACTUAL}/FI_{SETPOINT})],$$

where, $\beta$ is an empirically determined value between about 0.0 and about 4.0 and Z is a feed rate of an antifoulant material. A step-wise function may also be used to adjust antifoulant material feed rate.

| $FI_{ACTUAL}/FI_{SETPOINT}$ | Cascade Factor |
|---|---|
| <0.8 | 0.00 |
| 0.8–1.0 | 0.15 |
| 1.0–1.2 | 0.30 |
| 1.2–1.5 | 0.70 |
| >1.5 | 1.5 |

The values above are only examples of the cascade factors that may employed. Additionally, all values are approximate and may vary from the above without departing from the invention.

The cascade factors shown in the above table are dimensionless empirically determined factors based on field experience and laboratory data. The values may be a function of the product chemistry, system design and operating conditions. For example, in a heat exchange where the medium is on the shell side, the fluid velocity is normally very slow. If the heat duty of such a heat exchanger is such that the surface temperature is high, for example, greater than about 140° F., the potential for both fouling and corrosion is very high. The chemistry of some corrosion inhibitor products may, in high concentrations, actually increase the Fouling Index, while other products may have little or no effect. Therefore, we may use values of approximately 0.00, 0.10, 0.25, 0.5 and 0.8 for the cascade factors.

In some cases, such as when an aromatic azole is used specifically to inhibit corrosion of copper and copper bearing alloys, the cascade factor may be about 0.6, 1.0, 2.0, 4.0 and 8.0, respectively. This is partially due to the fact that normally, the corrosion rates are so low on such metals, for example, less than about 0.2 MPY, and that upsets, when they occur, are potentially severe. However, the aromatic azole has no deleterious effect on fouling. Another issue is cost effectiveness. For example, aromatic azoles are very expensive and normally used in very low dosages.

Elevated corrosion rates, which can cause significant damage to the system in their own right, may result in a release of excessive quantities of corrosion products such as ferrous and ferric hydroxides into the stream of cooling medium. Depending on the chemistry of the cooling medium, these materials may react with other ions in the stream of cooling medium to form foulants, may act as agglomerates of other suspended solids, such as silt, biomass, and process leaks, or be oxidized to form their own foulants (e.g., ferric oxide).

Therefore, the present invention may also include an algorithm to further increase the rate of feed of antifoulant when the corrosion rate exceeds predetermined value, and to remain at the higher rate for a period of time after the corrosion rate is reduced in order to inhibit further deposition.

According to the algorithm for increased corrosion, if $CORR_{MEASURED} > (G)(CORR_{SETPOINT})$, where G is a correction factor, then the algorithm governing material feed rate under conditions of normal corrosion will be further adjusted as follows:

$$Z = (X)\,[1+\beta(FI_{MEASURED}/FI_{SETPOINT})]+(\theta)(CORR_{MEASURED}/(G)\,CORR_{SETPOINT}),$$

where $\beta$ is a value between about 0.1 and about 8.0 and $\theta$ is a value between about 0.2 and about 2.0. The values of $\alpha$, $\beta$, and $\theta$ preferably are functions of the chemistries of the respective treatment materials.

The value of correction factor G in the above formula may be based on an assumption that a user would utilize a setpoint that is safely lower than the maximum allowable corrosion rate for the particular system. For example, correction factor G may have a value of from about 1.1 to about 2.0. A value of 1.1 would provide approximately a ten percent safety factor, whereas a value of about 2.0 would provide a safety factor of about one-hundred percent.

In one embodiment, correction factor G is about 1.5. Such a value assumes that the setpoint is set at about 66.7% of the maximum allowable corrosion value. If the setpoint were at about 80%, then the correction factor G would be about 1.25. Further, if the setpoint were at about 90%, then correction factor G would have a value of about 1.11. Therefore, it can be seen how a different value of correction factor could be derived.

$\theta$ is another cascade factor. It my be used to adjust the dispersant dosage when high corrosion rates occur. One reason for this is that corrosion products, such as ferrous and ferric ions subsequently react with the hydroxyl ion and then agglomerate other foulants such as suspended solids, hardness compounds and microflora to form additional fouling deposits. As with $\beta$, $\theta$ may be used to increase the dispersant feed rate due to an indicated increase in corrosion rate. The values for $\theta$ may be in the same range as the range of values for $\beta$ discussed above. Alternately, these factors may be split, using two separate dispersants, one as a supplement specifically directed at neutralizing the deleterious effects of excessive corrosion and the other just based on material balance and $\beta$.

An apparatus according to the present invention preferably includes means for measuring a flow rate of a make-up cooling system medium, means for measuring a conductivity of the make-up cooling system medium, means for measuring a conductivity of a recirculating cooling medium, and means for determining a treatment material feed rate based upon the formula:

$$X = \frac{(\text{make-up cooling medium flow rate})(\text{make-up cooling medium conductivity})(\Omega)}{(K)(\text{recirculating cooling medium conductivity})},$$

where X is a treatment feed rate of a treatment compound, $\Omega$ is a desired concentration of the treatment compound, and K is a constant. In this formula, if the values are measured according to the English system of measurement, the make-up flow rate may be measured in gallons per unit of time. The factor of 120,000 may be used to convert the flow rate to million pounds. Thus, X will be expressed in pounds per unit of time. In metric units, the flow rate may be measured in cubic meters per unit of time and X would then be in grams per unit of time. The value of K may be adjusted as described above to take into account the units that measurements of the other values in the equation are expressed in.

According to another embodiment, an apparatus according to the present invention may include means for measuring a blowdown flow rate rather than a make-up flow rate. Such an embodiment may also include means for determining a treatment material feed rate based upon the formula:

$$X = (\Omega)(\text{Cooling Medium Blowdown Flow Rate})/(120,000),$$

where X is a treatment material feed rate and $\Omega$ is a reference input to a control loop that regulates the treatment material feed rate.

Accordingly, an apparatus according to the invention that utilizes make-up flow rate may include one device for determining the Fouling Index and a second device that provides all of the other measurements and all control functions. The two devices could be included in a single unit.

A controller utilized according to the present invention may include a microprocessor. the microprocessor may be any type. For example, the microprocessor may be a "86" series microprocessor available from INTEL, including the PENTIUM processor and any other future INTEL processors. The apparatus may also use any available microprocessor. Examples of microprocessors that the invention may employ include microprocessors available from MOTOROLA, such as the 68000 line employed in Macintosh computers, POWER PC processors, or any other microprocessor available from any other manufacturer.

The microprocessor may include EPROM, EEPROM, and/or flash ROM technology for the software. Any other memory technology may also be utilized in an apparatus according to the present invention. Also, the apparatus may include a desirable amount of RAM. The RAM may be battery-backed.

A digital I/O board, an analog O/O board, a keypad decoder and a user interface may further be included in the apparatus. The interface could include a 20 key keypad and a 4 line, 40 character display. The apparatus may be enclosed in a single industrial weather proof enclosure.

An alternative embodiment could be based upon a programmable logic controller (PLC) with RAM and I/O capability similar to the embodiment described above. This alternative embodiment could include a multi-line or graphical user interface. Also, all components of the system could be included in a single apparatus.

A controller according to the invention may receive and use input signals from a corrosion monitor, a pH monitor, a conductivity monitor and, possibly, an Oxidation-Reduction-Potential monitor. Linear polarization resistance (LPR) technology may used to measure corrosion rate. An example of LPR technology is the CORRATER supplied by Rohrback Cosasco Systems. Conductivity and pH are measured by monitors that could be obtained from Foxboro Analytical, Signet Scientific, Great Lakes Instruments, Lakewood Instruments, Leeds & Northrup, Rosemount Analytical, Johnson-Yokagawa, and TBI Bailey Instruments. All of the above-listed companies are manufacturers of pH and conductivity instruments.

Input signals to the controller may supplied by generic sensor-transmitters and/or monitors. Examples of such sensors and monitors, are as those manufactured by Fisher-Rose, Foxboro Company, Johnson-Yokagawa, Hach Co., GF Signet Scientific, Rohrback Cosasco Systems and others, which determine parameters such as make-up cooling medium usage, cooling system blowdown, temperature(s) of the cooling medium at various points in the system, parameters of the cooling medium such as pH, conductivity, Oxidation-Reduction-Potential (ORP), turbidity, corrosion rate, and/or specific ions such as orthophosphate, molybdate, or silica. Any of said parameters may also be determined in the make-up cooling medium. In addition, an analog input signal may be obtained from a fouling monitor.

An apparatus according to the invention may also include an second microprocessor system similar to the microprocessor system described above with a different EPROM is used to determine fouling. This second microprocessor may incorporate an electronically controlled power controller for supplying a predetermined amount of heat at a constant heat flux across a heat transfer surface. A temperature measuring device may be located between the heater element and the heat transfer surface. A second temperature measuring device may be provided in the fluid stream entering the monitor.

Also, a flow monitor may be used to determine the flow rate of cooling medium entering the device. That flow may be controlled manually with a downstream valve or a combination of the downstream valve with an upstream pressure regulator, if line pressure varies significantly. The heated surface forms the inner surface of an annular flow assembly. Heat may supplied as electrical energy and the design assures that all heat will be transferred to the cooling medium as it passes across the heated surface. Flow and power may be adjusted to simulate actual plant operating conditions within a portion of a process heat exchanger which operates on the same cooling medium.

An example of a fouling monitor utilized in an apparatus according to the invention is the ONGUARD CFM-1000 monitor produced and marketed by Ashland Chemical Company, Drew Industrial Division of Boonton, N.J. An example of a controller that may be utilized in an apparatus according to the invention is the ONGUARD Alpha cooling medium controller also produced and marketed by Ashland Chemical Company, Drew Industrial Division of Boonton, N.J. The Alpha controller preferably measures makeup cooling medium flow rate, pH, conductivity, corrosion rate and ORP. However, it can also monitor many other parameters. Although, cooling medium flow rate, pH, conductivity, corrosion rate and ORP are the parameters that are particularly of interest in the invention.

According to one embodiment of the invention, a small, simple and less expensive device is utilized. A device according to this embodiment preferably produces a Fouling Index as a measure of fouling. The device preferably includes an integrated heater with at least one embedded thermocouple, a bulk cooling medium thermocouple, linear temperature transmitters, a sensitive flow measurement device, precision voltage and current transmitters, a means to precisely adjust and maintain constant power and an embedded logic controller to maintain the power, record the data, calculate set up conditions and output an analog signal proportionate to the fouling index. The Fouling Index may be communicated to a controller, either a programmable logic controller or an embedded logic controller may be used.

According to another embodiment, the systems of the present invention may be contained within a single housing. A further alternative embodiment may include a programmable logic controller (PLC) in place of an embedded logic controller.

Regardless of the embodiment of an apparatus according to the invention, the device preferably provides reproducible data.

In addition to corrosion and Fouling Index or Fouling Factor, oxidation-reduction potential (ORP) may also be a parameter that may be used to monitor and possibly control oxidants such as chlorine and bromine. Oxidation-Reduction-Potential has been used successfully to control the use of oxidizing microbicides in open recirculating cooling medium systems. ORP indicates the net result of all oxidizing and reducing agents in the stream of cooling medium. Maintaining an oxidation/reduction potential above a certain value, $\gamma$, may inhibit the growth of microorganisms both in the fluid and attached to solid surfaces.

Generally, $\gamma$ will fall between about +400 mV and about +600 mV, however, the optimum value of $\gamma$ may be site specific. In systems where intermittent dosing of oxidizing microbicides is used, a significant increase in the oxidizing potential of the stream of cooling medium generally occurs simultaneously with the injection of oxidizing microbicide.

The corrosivity of the cooling medium may also be affected by the treatment materials. For example, the corrosivity may change, depending upon the level of oxidant used, if any. The oxidant species may also affect corrosivity, as may the chemistry of the cooling medium. According to one example, a system that utilizes water including low level of dissolved solids as a cooling medium may become very corrosive when treated with excessive levels of chlorine. On the other hand, a highly buffered water used as a cooling medium treated with chlorine dioxide may not significantly increase the level of the water's corrosivity.

To protect the materials of construction from accelerated corrosion at such times, the corrosion inhibitor feed rate may also be adjusted based on the oxidation/reduction potential value. This is used primarily when critical components in the cooling medium system are fabricated of copper or copper bearing alloys and where an aromatic azole type material is used to specifically inhibit corrosion on copper bearing materials. In some cases, supplemental azole treatment may be employed. However, in many cases, the existing treatment levels are simply raised.

Traditionally, such adjustment is accomplished by simply energizing the azole feed adjustment simultaneously with the microbicide feed. However, the increase in ORP does not occur instantaneously. Rather it increases as a function of the increased concentration of oxidizing microbicide.

It may take as much as 2 to 3 hours for the concentration to reach a level at which the additional corrosion inhibition is required. In addition, the elevated ORP remains for some, usually significant, period of time after the injection ceases. Therefore, controlling the elevation of azole injection as a function of ORP is significantly more cost effective than the traditional means.

In this case where $ORP_{ACTUAL} > ORP_{BREAKPOINT}$ then, $$Azole = (X) + (Azole_{ORP}) + (Azole_{CORR})$$

where, $Azole_{ORP}$ = the amount of azole added based on a site specific change in ORP, and $Azole_{CORR}$ = the amount of additional azole required to overcome increased corrosion based on LPR technology applied to copper bearing electrodes.

The present invention also contemplates the use of other parameters for controlling chemical treatment and quality of cooling medium in cooling systems. For example, fouling factor (FF) may also be utilized in the methods of the present invention.

HYPOTHETICAL EXAMPLE

The following is a hypothetical example of an application of the present invention to a hypothetical cooling system. In the example, the cooling system is subject to contamination from a number of sources. For example, among other sources, contamination may originate from petrochemical process contamination, airborne contamination from immediate operating unit(s), airborne contamination from nearby production facilities, and/or environmental conditions such as ambient temperature swings, humidity changes as well as wind speed and direction. Such environmental conditions are typical of many CPI and HPI facilities.

Prior to installation of a control system according to the present invention, the throughput or a combination of throughput and product quality of the production process was limited by cooling water. Both throughput and product quality can be adversely effected by the ability of the cooling system to reject heat, which is normally the result of fouling aggravated by high ambient temperatures. For example, process leaks went mostly undetected for extended periods, resulting in excessive corrosion, biomass accumulation and fouling. Additionally, chemical treatment was base loaded, with a specified amount added continuously over each 24 hour period. Changes in treatment dosages were made at frequencies varying between daily and weekly depending on laboratory analyses.

The preliminary stages of developing the present invention included developing an on-line means to detect process leaks and airborne contamination, both of which may accelerate growth of biomass. Additionally, some process leaks may accelerate corrosion. Biomass may agglomerate on wetted surfaces in the cooling system and can result in under deposit corrosion, both from acid secretion by the microbes themselves and by causing a differential oxygen concentration between the covered surface and the surrounding surfaces.

According to the example, chlorine was continuously added to the cooling system at a preset constant rate to control biomass production. When process leaks occurred, the ORP was found to decrease. Prior experience at this site has shown that, when ORP is maintained between about 480 and about 550 mV, biomass is brought into control and corrosion rates are reduced. Increasing the feed of chlorine was found to have limited effect. However, when chlorine dioxide was used as the supplement, the ORP increased.

The water used to makeup to this system is of inconsistent quality with respect to hardness and alkalinity. Excessive hardness in the circulating water may cause precipitation of hardness salts as scale. Operating the system with low cycles of concentration may result in excessive water consumption and a decrease in the cost-effectiveness of the treatment program.

The first building block of the Performance-Based Control System was the to add mass balance as a factor in controlling pH and conductivity. Mass balance was used to maintain a predetermined concentration of corrosion inhibitor and fouling inhibitor in the circulating water at all times.

The second building block of the Performance-Based Control System was the addition of online ORP measurement. The actual ORP was compared with predetermined process specifications to automatically turn on and turn off the feed of chlorine dioxide.

For example, when the ORP dropped below 400 mV, chlorine dioxide feed was initiated for a period of two hours. However, if within that period, the ORP increased to 580 mV, its feed would be terminated. If the ORP drops below 300 mV, the control system transmits an alarm to advise the process operators that a major leak has occurred and that human intervention is required to find and fix it. If, after two hours, the ORP had not increased to at least 500 mV, an additional two hour feed period is initiated and an alarm is triggered to advise the process operators that human intervention may be required.

The third building block of the Performance-Based Control System is the addition of fouling to the above-described variables. Normally, the cooling system was run with a minimal potential for fouling, except when process leaks occurred. One goal of the new control system of the present invention is to optimize the cooling process by reducing water consumption. This increased the potential for fouling from both scale formation and biomass.

A process specification was established based on analysis of the design and operation of the plant's heat exchangers. The feed of fouling inhibitor was base-lined to maintain fouling at or below about 80% of the process specification as determined by the fouling monitor. Logic was added to the control system to increase the fouling inhibitor feed should the fouling monitor detect an accumulation of fouling exceeding that figure.

The first reduction of this invention used a stepwise incremental adjustment with steps set at about 1.15, 1.3, 1.7 and 2.5 times the base feed rate at about 80%, 100%, 120% and 150% of the process specification. In addition, once the feed rate was increased, it would stay at the higher level for a minimum of about 24 hours before being allowed to decrease due to a reduction in fouling.

A further building block of the Performance-Based Control System according to the present invention was the addition of on-line corrosion rate determination to the above-discussed parameters. Since corrosion is interrelated with fouling and biofouling, or biomass agglomeration, this added a new dimension to the control system.

At the starting point, after initiation of the control system, the cooling water system operated within process specifications, a situation that continued for some period of time. Among the process specifications were:

| Parameter | Specifications |
| --- | --- |
| pH | 7.4–7.7 |
| ORP | 480–550 mV |
| Corrosion Rate | 3.0 MPY (max.) |
| Fouling Index | 150 (max.) |
| Conductivity | 2200–2400 $\mu$S |

At time X, the ORP monitor detected a drop in ORP from about 500 to about 350 mV over the course of several minutes. The drop triggered initiation of chlorine dioxide feed, which, after several additional minutes, caused the ORP to first level off and then start to rise.

At about X+3 minutes, the pH dropped below about 7.4 and acid feed was terminated.

By about X+10 minutes, the pH had dropped to about 6.9 and the corrosion rate had jumped to about 3.5 MPY. Corrosion inhibitor feed was increased to about 1.4 times base feed level, by selecting the Cascade Factor $\alpha$ according to the table above. At the same time, the fouling monitor detected a rise in Fouling Index, though its value was still well below the specified maximum.

At about X+20 minutes, the pH was still at about 6.9 and the control system increased the rate of blowdown by about 20% to deconcentrate the circulating water, replacing it with fresh makeup.

By about X+40 minutes, the pH had risen above about 7.0 and the ORP had begun to rise.

By about X+50 minutes, the corrosion rate reached about 4.6 MPY, about 53% above the setpoint and the corrosion inhibitor feed rate had been increased to about 1.7 times its base rate, as corrected by the Cascade Factor $\beta$, selected according to the table above. The elevated corrosion rate caused the fouling inhibitor feed rate to be increased to about 1.17 times base rate, as corrected by the Cascade Factor $\theta$, calculated according to the previously discussed equation, where $\theta=0.9\times\beta$, G=1.3 and the factors $FI_{MEASURED}/FI_{SETPOINT}$ and $CORR_{MEASURED}/(G\times CORR_{SETPOINT})$ are based on the tables above showing values for Cascade Factors $\alpha$ and $\beta$, adjusted as noted above.

By about X+90, the Fouling Index reached a level exceeding about 80% of the setpoint and the fouling inhibitor feed rate was increased again. This increased the feed rate an additional about 1.15 times the base rate for a total feed of about 1.30 times the base rate.

At about X+120 minutes, the ORP had increased from a low of about 330 mV to about 440 mV, but was still not within the process specifications. An alarm was triggered requesting operations personnel to locate and correct the process leak.

By about X+170 minutes, the ORP had risen above about 480 mV, the pH was at about 7.5 and the conductivity was at about 2050 $\mu$S. The blowdown rate was reduced to about 90% of setpoint.

By about X+220, the corrosion rate had decreased to about 3.0 and the Fouling Index had stabilized at about 92% of setpoint. The pH had risen to about 7.6 and acid feed resumed at normal rate. The conductivity was at about 2210 $\mu$S and blowdown adjusted to about 97% of setpoint.

At about X+240, chlorine dioxide feed was terminated.

By about X+6 hours, the corrosion rate was again below about 2 MPY, the ORP was at about 520 mV, the conductivity at about 2290 $\mu$S and Fouling Index was down to about 75% of setpoint.

At about X+24 hours, the fouling inhibitor feed rate was decreased back to about 1.15 times the base rate, based upon the calculations and selection of the Cascade Factor $\beta$. The inhibitor feed rate remained at this level for about another 24 hours, until it was returned to the base rate. The corrosion inhibitor feed rate was decreased to the base rate.

Figure 1:
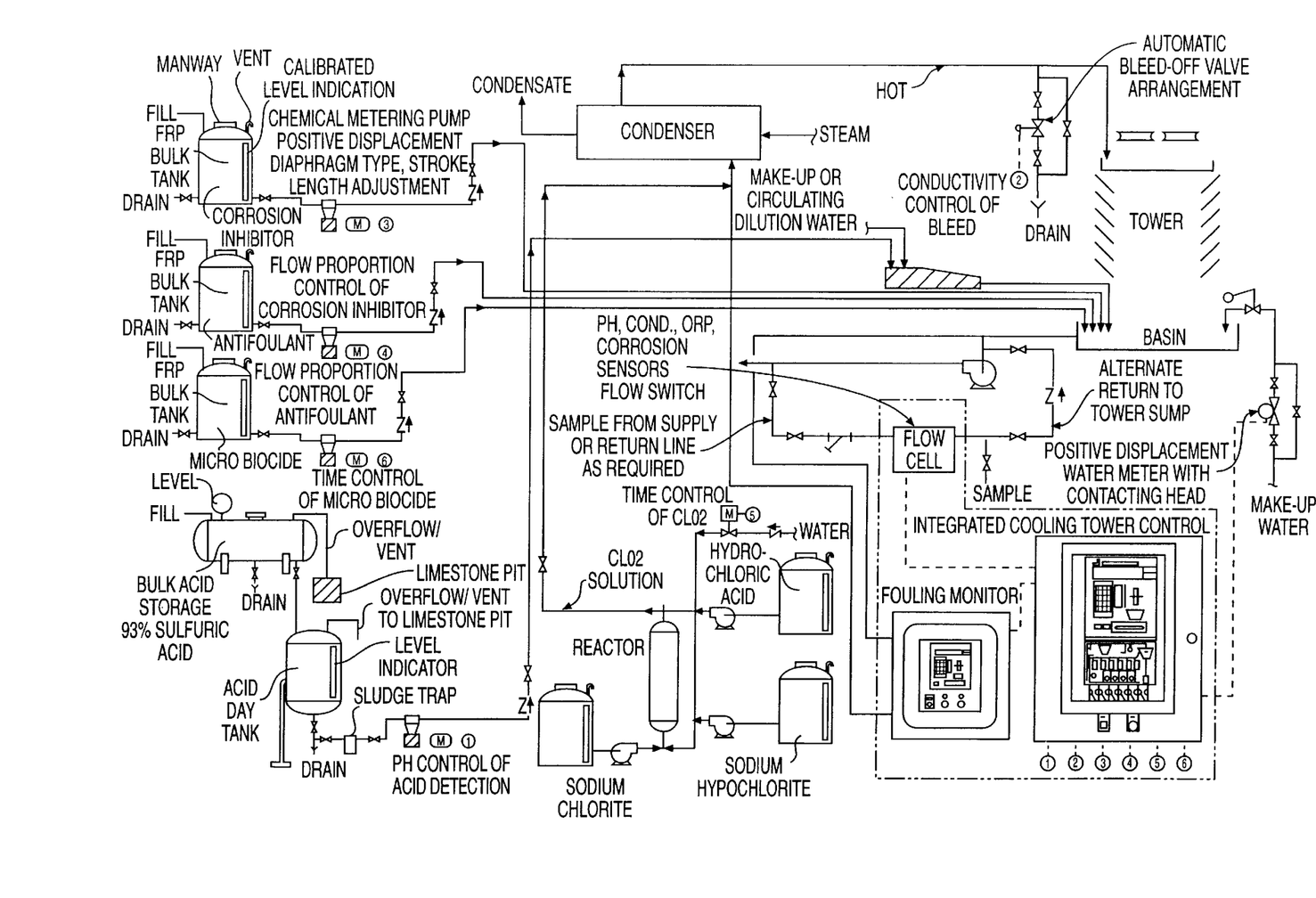
FIG. 1 is a schematic representation of an embodiment of a cooling system including an embodiment of a control system according to the present invention integrated within.

FIG. 1 shows an embodiment of a control system according to the present invention integrated into a complete cooling system. As shown in the box 1, the control system may include pH, conductivity and ORP monitors. The monitors may be any commercially available from several sources. For example, such monitors may be obtained from Rosemount Analytical.

The system may also include a corrosion monitor. Any commercially available corrosion monitor of the type applicable to this invention may be employed. For example, Rohrback Cosasco Systems manufactures a corrosion monitor.

The numbers at the bottom of the integrated cooling tower control shown in FIG. 1 refer to level sensors on the bulk tanks. Fouling data may be provided by an ONGUARD CFM-1000 fouling monitor. Another example of a monitor that may provide fouling data is a P-U-L-S-E analyzer. FIG. 1 does not show interfaces between the control system of the present invention and the plant's distributed control system and with remote computers, hard-wired, by phone or various other existing telemetry methods. A control system according to the invention may be furnished as several separate components. Alternatively, the control system may be provided in the form of a single physical package.

In this disclosure, there is shown and described only the preferred embodiments of the invention, but, as aforementioned it is to be understood that the invention is capable of use in various other combinations and environments and is capable of changes or modifications within the scope of the inventive concept as expressed herein.

We claim:

1. A method for detecting and controlling cooling system characteristics, said method comprising the steps of:

measuring a flow rate of make-up cooling medium;

measuring a conductivity of said make-up cooling medium;

measuring a conductivity of a recirculating cooling medium; determining a treatment compound feed rate based upon the following formula:

$$X = \frac{(\text{make-up cooling medium flow rate})(\text{make-up cooling medium conductivity})(\Omega)}{(K)(\text{recirculating cooling medium conductivity})},$$

where X is a treatment feed rate of a treatment compound, $\Omega$ is a desired concentration of the treatment compound, and K is a constant;

measuring a corrosion rate of the recirculating cooling medium;

determining a desired corrosion rate of the recirculating cooling medium;

calculating a feed rate of a corrosion inhibitor according to the following formula:

$$Y=(X)[1+\alpha(CORR_{MEASURED}/CORR_{SETPOINT})],$$

where Y is the feed rate of the corrosion inhibitor, X is as defined above, $CORR_{MEASURED}$ and $CORR_{SETPOINT}$ respectively represent a measured corrosion rate and a set value for corrosion rate, and $\alpha$ is a cascade factor that varies in a step-wise manner depending upon the value of $CORR_{MEASAURED}/CORR_{SETPOINT}$ and has a value between about 0.0 and about 8.0; and feeding a corrosion inhibitor at said corrosion inhibitor feed rate.

2. A method according to claim 1, wherein when $CORR_{MEASURED}/CORR_{SETPOINT}$ is less than 0.75, $\alpha$ is about 0.00.

3. A method according to claim 1, wherein when $CORR_{MEASURED}/CORR_{SETPOINT}$ is between about 0.75 and about 0.99, $\alpha$ is about 0.15.

4. A method according to claim 1, wherein when $CORR_{MEASURED}/CORR_{SETPOINT}$ is between about 1.00 and about 1.50, $\alpha$ is about 0.40.

5. A method according to claim 1, wherein when $CORR_{MEASURED}/CORR_{SETPOINT}$ is between about 1.50 and about 3.00, $\alpha$ is about 1.00.

6. A method according to claim 1, wherein when $CORR_{MEASURED}/CORR_{SETPOINT}$ is greater that about 2.00, $\alpha$ is about 2.00.

7. A method according to claim 1, further comprising the steps of:

measuring a fouling index of the recirculating cooling medium, wherein fouling index is calculated according to the formula:

$$FI=(A)\{[(T_w-T_b)/Power-B]_c-[(T_w-T_b)/Power-B]_i\}+J,$$

where
FI=Fouling Index
$J=(C)[(T_b)_c-(T_b)_i]+(D)(F_c-F_i)+(E)(POWER_c-POWER_i)$
F=flow rate of cooling medium,
A, B, C, D, E, and J=correction factors,
Power=power level associated with a wall of the cooling system as heated by a heat source cooled by the cooling system,
$T_b$=bulk fluid temperature of the cooling medium,
$T_w$=wall temperature of a wall of the cooling system,
i represents initial readings of the variables in the formulas for FI and J, and
c represents current readings of the variables in the formulas for FI and J; and determining a desired fouling index of the recirculating cooling medium;

wherein if $CORR_{MEASURED}>(G)CORR_{SETPOINT}$, where $CORR_{MEASURED}$ and $CORR_{SETPOINT}$ respectively represent a measured corrosion rate and a set value for corrosion rate, a feed rate of a fouling inhibitor is calculated according to the following formula:

$$Z=(X)[1+\beta(FI_{MEASURED}/FI_{SETPOINT})]+(\theta)(CORR_{MEASURED}/(G)CORR_{SETPOINT}),$$

where
Z is a feed rate of a fouling inhibitor, X is as defined above, $FI_{MEASURED}$ and $FI_{SETPOINT}$ respectively represent a measured value and a set value for Fouling Index, $\beta$ is a cascade factor that varies in a step-wise manner depending upon the value of $FI_{MEASURED}/FI_{SETPOINT}$ and has a value between about 0.0 and about 8.0 and $\theta$ is a cascade factor that varies in a step-wise manner depending upon the value of $CORR_{MEASURED}/(G)CORR_{SETPOINT}$ and has a value between about 0.2 and about 2.0.; and G is a correction factor.

8. A method according to claim 1, wherein K is about 120,000 or about 1,000.

9. A method for detecting and controlling cooling system characteristics, said method comprising the steps of:

measuring a flow rate of make-up cooling medium;

measuring a conductivity of said make-up cooling medium;

measuring a conductivity of a recirculating cooling medium;

determining a treatment compound feed rate based upon the following formula:

$$X = \frac{\text{(make-up cooling medium flow rate)}\text{(make-up cooling medium conductivity)}(\Omega)}{(K)\text{(recirculating cooling medium conductivity)}},$$

where X is a treatment feed rate of a treatment compound, $\Omega$ is a desired concentration of the treatment compound, and K is a constant;

measuring a Fouling Index of the recirculating cooling medium, wherein said Fouling Index is calculated according to the formula:

$$FI=(A)\{[(T_w-T_b)/Power-B]_c-[(T_w-T_b)/Power-B]_i\}+J,$$

where
FI=Fouling Index
$J=(C)[(T_b)_c-(T_b)_i]+(D)(F_c-F_i)+(E)(POWER_c-POWER_i)$
F=flow rate of cooling medium,
A, B, C, D, E, and J=correction factors,
Power=power level associated with a wall of the cooling system as heated by a heat source cooled by the cooling system,
$T_b$=bulk fluid temperature of the cooling medium,
$T_w$=wall temperature of a wall of the cooling system,
i represents initial readings of the variables in the formulas for FI and J, and
c represents current readings of the variables in the formulas for FI and J;

determining a desired fouling index of the recirculating cooling medium;

calculating a feed rate of a fouling inhibitor according to the following formula:

$$Z=(X)[1+\beta(FI_{MEASURED}/FI_{SETPOINT})],$$

where Z is a feed rate of a fouling inhibitor, X is as defined above, $FI_{MEASURED}$ and $FI_{SETPOINT}$ respectively represent a measured value and a set value for Fouling Index, and $\beta$ is a cascade factor that varies in a step-wise manner depending upon the value of $FI_{MEASURED}/FI_{SETPOINT}$ and has a value between about 0.0 and about 8.0; and feeding a fouling inhibitor at said fouling inhibitor feed rate.

10. A method according to claim 9, wherein when $FI_{MEASURED}/FI_{SETPOINT}$ is less than about 0.8, $\beta$ is about 0.00.

11. A method according to claim 9, wherein when $FI_{MEASURED}/FI_{SETPOINT}$ is between about 0.8 and about 1.0, $\beta$ is about 0.15.

12. A method according to claim 9, wherein when $FI_{MEASURED}/FI_{SETPOINT}$ is between about 1.0 and about 1.2, β is about 0.30.

13. A method according to claim 9, wherein when $FI_{MEASURED}/FI_{SETPOINT}$ is between about 1.2 and about 1.5, β is about 0.70.

14. A method according to claim 9, wherein when $FI_{MEASURED}/FI_{SETPOINT}$ is greater than about 1.5, β is about 1.50.

15. A method according to claim 9, wherein A is between about 0.002 and about 1000, B is between about 0.167/F and about 1/F, C is about 0.321, D is about 1.432, and E is about 0.0665.

16. A method according to claim 15, wherein A is about 400, B is about 0.25/F.

17. A method according to claim 15, wherein A is between about 0.002 and about 1000, B is between about 1/F and about 0.167/F, C is about 0.321, D is about 1.432, E is about 0.0665 and G is between about 1.11 and about 1.5.

18. A method according to claim 17, wherein A is about 400, B is about 0.25/F, and G is about 1.5.

19. A method for detecting and controlling cooling system characteristics, said method comprising the steps of:
 measuring a flow rate of make-up cooling medium;
 measuring a conductivity of said make-up cooling medium;
 measuring a conductivity of a recirculating cooling medium;
 determining a treatment feed rate based upon the following formula:

$$X = \frac{\text{(make-up cooling medium flow rate)}\text{(make-up cooling medium conductivity)}(\Omega)}{(K)\text{(recirculating cooling medium conductivity)}},$$

where X is a treatment feed rate of a treatment compound, Ω is a desired concentration of the treatment compound, and K is a constant;
 feeding a treatment compound at said treatment feed rate;
 measuring a corrosion rate of the recirculating cooling medium;
 determining a desired corrosion rate of the recirculating cooling medium;
 calculating a feed rate of a corrosion inhibitor according to the following formula:

$$Y = (X)[1 + \alpha(CORR_{MEASURED}/CORR_{SETPOINT})],$$

where Y is a feed rate of a corrosion inhibitor, $CORR_{MEASURED}$ and $CORR_{SETPOINT}$ respectively represent a measured corrosion rate and a set value for corrosion rate, α is a cascade factor that varies in a continuous manner depending upon the value of $CORR_{MEASURED}/CORR_{SETPOINT}$ and has a value between about 0.0 and about 8.0; and
 feeding a corrosion inhibitor at said corrosion inhibitor feed rate.

20. A method for detecting and controlling cooling system characteristics, said method comprising the steps of:
 measuring a flow rate of make-up cooling medium;
 measuring a conductivity of said make-up cooling medium;
 measuring a conductivity of a recirculating cooling medium;
 determining a treatment feed rate based upon the following formula:

$$X = \frac{\text{(make-up cooling medium flow rate)}\text{(make-up cooling medium conductivity)}(\Omega)}{(K)\text{(recirculating cooling medium conductivity)}},$$

where X is a treatment feed rate of a treatment compound, Ω is a desired concentration of the treatment compound, and K is a constant;
 feeding a treatment compound at said treatment feed rate;
 measuring a Fouling Index of the recirculating cooling medium, wherein said Fouling Index is calculated according to the formula:

$$FI = (A)\{[(T_w - T_b)/Power - B]_c - [(T_w - T_b)/Power - B]_i\} + J,$$

where
 FI = Fouling Index,
 $J = (C)\ [(T_b)_c - (T_b)_i)] + (D)\ (F_c - F_i) + (E)\ (POWER_c - POWER_i)$
 F = flow rate of cooling medium,
 A, B, C, D, E, and J = correction factors,
 Power = power level associated with a wall of the cooling system as heated by a heat source cooled by the cooling system,
 $T_b$ = bulk fluid temperature of the cooling medium,
 $T_w$ = wall temperature of a wall of the cooling system,
 i represents initial readings of the variables in the formulas for FI and J, and
 c represents current readings of the variables in the formulas for FI and J;
 determining a desired fouling index of the recirculating cooling medium;
 calculating a feed rate of a fouling inhibitor according to the following formula:

$$Z = (X)[1 + \beta(FI_{MEASURED}/FI_{SETPOINT})],$$

where Z is a feed rate of a fouling factor, where $FI_{MEASURED}$ and $FI_{SETPOINT}$ respectively represent a measured value and a set value for Fouling Index, β is a cascade factor that varies in a continuous manner depending upon the value of $FI_{MEASURED}/FI_{SETPOINT}$ and has a value between about 0.0 and about 8.0; and
 feeding a fouling inhibitor at said fouling inhibitor feed rate.

21. An apparatus for detecting and controlling conditions in a cooling system, comprising:
 means for measuring a flow rate of a make-up cooling system medium;
 means for measuring a conductivity of the make-up cooling system medium;
 means for measuring a conductivity of a recirculating cooling medium;
 means for determining a treatment material feed rate based upon the formula $$X = \frac{\text{(make-up cooling medium flow rate)}\text{(make-up cooling medium conductivity)}(\Omega)}{(K)\text{(recirculating cooling medium conductivity)}},$$

where X is a treatment feed rate of a treatment compound, Ω is a desired concentration of the treatment compound, and K is a constant;
 means for feeding a treatment material into the cooling system at said determined feed rate;

means for measuring a corrosion rate of the recirculating cooling medium;

means for determining a desired corrosion rate of the recirculating cooling medium; and means for calculating a feed rate of a corrosion inhibitor according to the following formula:

$$Y=(X)[1+\alpha(CORR_{MEASURED}/CORR_{SETPOINT})],$$

where Y is a feed rate of a corrosion inhibitor, where $CORR_{MEASURED}$ and $CORR_{SETPOINT}$ respectively represent a measured corrosion rate and a set value for corrosion rate, $\alpha$ a cascade factor that varies in a step-wise manner depending upon the value of $CORR_{MEASURED}/CORR_{SETPOINT}$ and has is a value between about 0.1 and about 8.0.

22. A method according to claim 21, wherein A is between about 0.002 and about 1000, B is between about 0.167/F and about 1/F, C is about 0.321, D is about 1.432, and E is about 0.0665.

23. A method according to claim 21, wherein K is about 120,000 or about 1,000.

24. An apparatus for detecting and controlling conditions in a cooling system, comprising:

means for measuring a flow rate of a make-up cooling system medium;

means for measuring a conductivity of the make-up cooling system medium;

means for measuring a conductivity of a recirculating cooling medium;

means for determining a treatment material feed rate based upon the formula $$X = \frac{\text{(make-up cooling medium flow rate)} \text{(make-up cooling medium conductivity)}(\Omega)}{(K)\text{(recirculating cooling medium conductivity)}},$$

where X is a treatment feed rate of a treatment compound, $\Omega$ is a desired concentration of the treatment compound, and K is a constant;

means for feeding a treatment material into the cooling system at said determined feed rate;

means for measuring a fouling index of the recirculating cooling medium, wherein fouling index is calculated according to the formula:

$$FI=(A)\{[(T_w-T_b)/Power-B/F]_c-[(T_w-T_b)/Power-B/F]_i\}+J,$$

where
FI=Fouling Index,
$J=(C)[(T_b)_c-(T_b)_i)]+(D) (F_c-F_i)+(E) (POWER_c-POWER_i)$
F=flow rate of cooling medium,
A, B, C, D, E, and J=correction factors,
Power=power level associated with a wall of the cooling system as heated by a heat source cooled by the cooling system,
$T_b$=bulk fluid temperature of the cooling medium,
$T_w$=wall temperature of a wall of the cooling system,
i represents initial readings of the variables in the formulas for FI and J, and
c represents current readings of the variables in the formulas for FI and J;

means for determining a desired fouling index of the recirculating cooling medium; and means for calculating a feed rate of a fouling inhibitor according to the following formula:

$$Z=(X)[1+\beta(FI_{MEASURED}/FI_{SETPOINT})],$$

where Z is a feed rate of a fouling inhibitor, $FI_{MEASURED}$ and $FI_{SETPOINT}$ respectively represent a measured value and a set value for Fouling Index, $\beta$ is a cascade factor that varies in a step-wise manner depending upon the value of $FI_{MEASURED}/FI_{SETPOINT}$ and has a value between about 0.0 and about 8.0.

25. A method according to claim 24, wherein A is about 400, B is about 0.25/F.

26. An apparatus for detecting and controlling conditions in a cooling system, comprising:

means for measuring a flow rate of a make-up cooling system medium;

means for measuring a conductivity of the make-up cooling system medium;

means for measuring a conductivity of a recirculating cooling medium;

means for determining a treatment material feed rate based upon the formula $$X = \frac{\text{(make-up cooling medium flow rate)} \text{(make-up cooling medium conductivity)}(\Omega)}{(K)\text{(recirculating cooling medium conductivity)}},$$

where X is a treatment feed rate of a treatment compound, $\Omega$ is a desired concentration of the treatment compound, and K is a constant;

means for feeding a treatment material into the cooling system at said determined feed rate;

means for measuring a corrosion rate of the recirculating cooling medium;

means for determining a desired corrosion rate of the recirculating cooling medium;

means for measuring a fouling index of the recirculating cooling medium, wherein fouling index is calculated according to the formula:

$$FI=(A)\{[(T_w-T_b)/Power-B/F]_c-[(T_w-T_b)/Power-B/F]_i\}+J,$$

where
FI=Fouling Index,
$J=(C)[(T_b)_c-(T_b)_i)]+(D) (F_c-F_i)+(E) (POWER_c-POWER_i)$
F=flow rate of cooling medium,
A, B, C, D, E, and J=correction factors,
Power=power level associated with a wall of the cooling system as heated by a heat source cooled by the cooling system,
$T_b$=bulk fluid temperature of the cooling medium,
$T_w$=wall temperature of a wall of the cooling system,
i represents initial readings of the variables in the formulas for FI and J, and
c represents current readings of the variables in the formulas for FI and J; and means for determining a desired fouling index of the recirculating cooling medium;

wherein if $CORR_{MEASURED}>(G)CORR_{SETPOINT}$, wherein G is a correction factor, said determining means determines a feed rate of a fouling inhibitor according to the following formula:

$$Z=(X)[1+\beta(FI_{MEASURED}/FI_{SETPOINT})]+(\theta)(CORR_{MEASURED}/$$

$(G)CORR_{SETPOINT}$), where Z is a feed rate of a fouling inhibitor, β is a cascade factor that varies in a step-wise manner depending upon the value of $FI_{MEASURED}/FI_{SETPOINT}$, where $FI_{MEASURED}$ and $FI_{SETPOINT}$ respectively represent a measured value and a set value for Fouling Index, and has a value between about 0.0 and about 8.0 and θ is a cascade factor that varies in a step-wise manner depending upon the value of $CORR_{MEASURED}/(G)CORR_{SETPOINT}$, $CORR_{MEASURED}$ and $CORR_{SETPOINT}$ respectively represent a measured corrosion rate and a set value for corrosion rate, and has a value between 0.2 and 2.0.

27. A method according to claim 26, wherein A is between about 0.002 and about 1000, B is between about 0.167/F and about 1/F, C is about 0.321, D is about 1.432, E is about 0.0665 and G is between about 1.11 and about 1.5.

28. A method according to claim 26, wherein A is about 400, B is about 0.25/F, and G is about 1.5.

* * * * *